United States Patent [19]
McDowell et al.

[11] Patent Number: 5,905,568
[45] Date of Patent: May 18, 1999

[54] STEREO IMAGING VELOCIMETRY

[75] Inventors: Mark McDowell, Cleveland; Thomas K. Glasgow, Rocky River, both of Ohio

[73] Assignee: The United States of America as represented by the Administrator of the National Aeronautics and Space Administration, Washington, D.C.

[21] Appl. No.: 08/990,265

[22] Filed: Dec. 15, 1997

[51] Int. Cl.⁶ .............................. G01P 3/36; G01N 21/00; H04N 7/18
[52] U.S. Cl. .............................. 356/28; 348/135; 356/337
[58] Field of Search ....................... 356/28, 337; 348/135

[56] References Cited

U.S. PATENT DOCUMENTS

| | | |
|---|---|---|
| 4,337,049 | 6/1982 | Connelly . |
| 4,709,580 | 12/1987 | Butts, Jr. et al. . |
| 4,729,109 | 3/1988 | Adrian et al. . |
| 4,919,536 | 4/1990 | Komine . |
| 4,988,191 | 1/1991 | Adrian et al. . |
| 5,011,278 | 4/1991 | Farrell . |
| 5,110,204 | 5/1992 | Miles et al. . |
| 5,333,044 | 7/1994 | Shaffer . |
| 5,396,331 | 3/1995 | Kitoh et al. . |
| 5,440,144 | 8/1995 | Raffel et al. . |
| 5,491,642 | 2/1996 | Wormell et al. . |
| 5,532,814 | 7/1996 | Cha . |
| 5,610,703 | 3/1997 | Raffel et al. . |

*Primary Examiner*—Stephen C. Buczinski
*Attorney, Agent, or Firm*—Kent N. Stone

[57] ABSTRACT

A system and a method for measuring three-dimensional velocities at a plurality of points in a fluid employing at least two cameras positioned approximately perpendicular to one another. The cameras are calibrated to accurately represent image coordinates in world coordinate system. The two-dimensional views of the cameras are recorded for image processing and centroid coordinate determination. Any overlapping particle clusters are decomposed into constituent centroids. The tracer particles are tracked on a two-dimensional basis and then stereo matched to obtain three-dimensional locations of the particles as a function of time so that velocities can be measured therefrom. The stereo imaging velocimetry technique of the present invention provides a full-field, quantitative, three-dimensional map of any optically transparent fluid which is seeded with tracer particles.

20 Claims, 6 Drawing Sheets

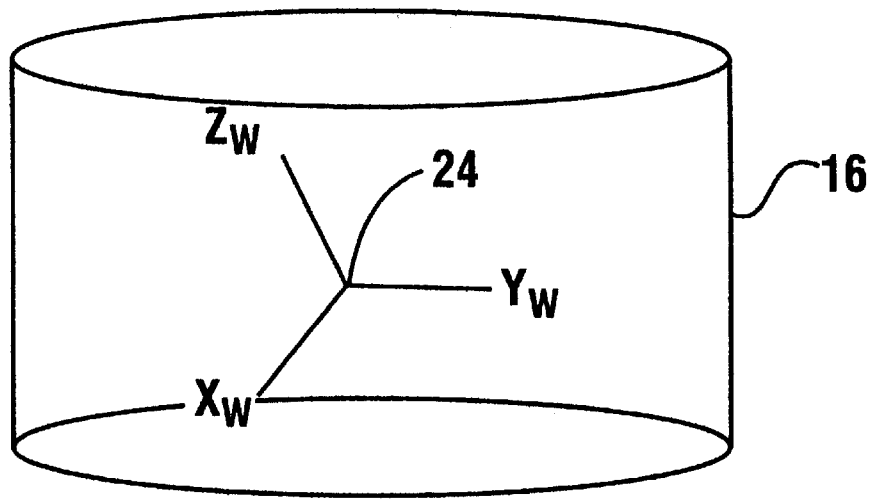
FIG. 2A
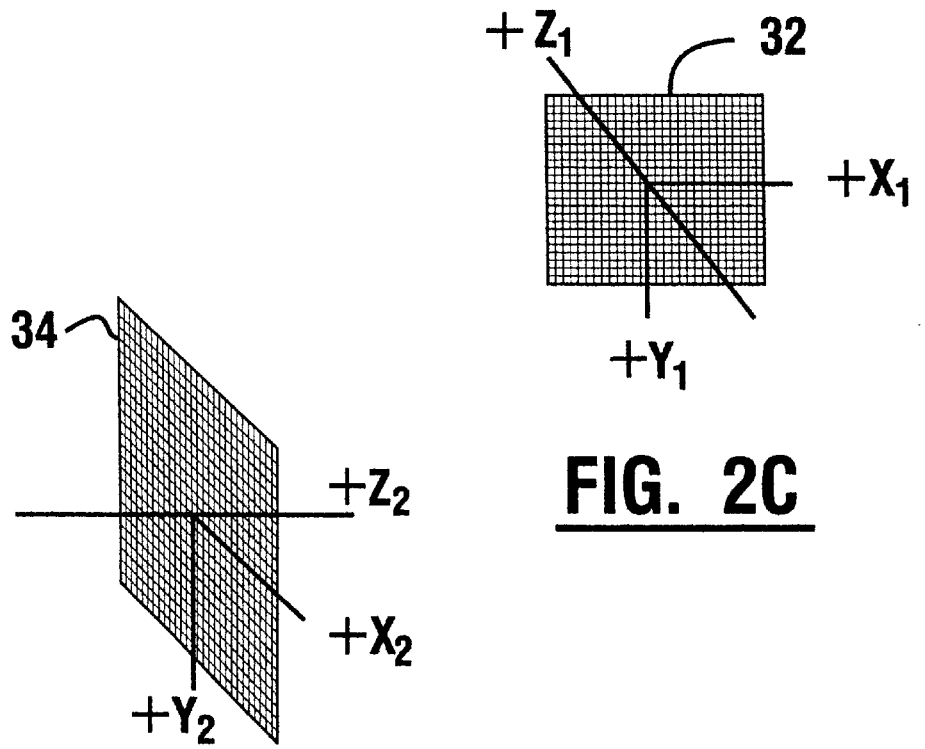
FIG. 2C
FIG. 2B

STEREO IMAGING VELOCIMETRY

ORIGIN OF THE INVENTION

The invention described herein was made by employees of the United States Government and may be manufactured and used by or for the Government for Government purposes without the payment of any royalties thereon or therefor.

TECHNICAL FIELD

This invention relates to stereo imaging velocimetry. Specifically, this invention relates to a system and method for measuring three-dimensional velocities at a plurality of points in a fluid seeded with tracer particles.

BACKGROUND ART

Stereo imaging velocimetry seeks to provide a three-dimensional measurement of the velocity of a fluid. As early as 1973, Elkins et al, in an article titled "Evaluation of Stereoscopic Trace Particle Records of Turbulent Flow Fields," Review of Scientific Instruments, Vol. 48, No. 7, pp. 738–746, (1977) reported an early stereo imaging system using cinematography equipment coupled with an electronic digitizer to track several hundred particles in a turbulent flow. Other early efforts employed a multi-colored approach which allowed higher seeding densities since particles could be separated into groups according to color.

One effort applied this technology to an approved understanding of internal combustion based completely on digital technology., A. A. Adamczyk and L. Ramai, "Reconstruction of a 3-Dimensional Flow Field from Orthogonal Views of Seed Track Video Images," Experiments in Fluids, 6, pp. 380–386, (1988), and "2-Dimensional Particle Tracking (PTV): Technique and Image Processing Algorithms," Experiments in Fluids, Vol. 6, (1988).

Another approach in Canada included performing stereo matching on particles, then tracking the three-dimensional locations in time to reproduce particle motion, R. G. Racca and J. M. Dewey, "A Method for Automatic Particle Tracking in a Three-Dimensional Flow Field," Experiments in Fluids, 6, pp. 25–32, (1988). Most researchers do the opposite, first tracking in two dimensions, then stereo matching the tracks to obtain the third dimension.

Guezennec, et al. have developed a commercially viable instrument that provides qualitative but not quantitative three-dimension results, Y. G. Guezennec, et al. "Algorithms for Fully Automated Three Dimensional Tracking Velocimetry Experiments in Fluids," Experiments in Fluids, 4, (1993).

Raffel, et al. patents, U.S. Pat. No. 5,440,144 and U.S. Pat. No. 5,610,703, disclose a method and an apparatus for measurement of three-dimensional flow velocities. U.S. Pat. No. 5,440,144 relates to a pulsed light method for particle image velocimetry (PIV). When using a pulsed light laser technique, one disadvantage is the complexity of the system while another disadvantage is the small area of the field of view. U.S. Pat. No. 5,610,703 relates to a digital particle image velocimetry (DPIV) method. This patent also describes the use of a pulsed laser light source, but does describe using a CCD camera with a laser source and an electro-mechanical shutter controlled by the DPIV timer box.

U.S. Pat. No. 5,491,642 describes a PIV system which uses pulsed-laser techniques. This patent describes recording the image with a charge coupled device (CCD) camera.

U.S. Pat. No. 4,919,536 describes a system for measuring velocity field fluid flow utilizing a Laser-Doppler spectral image converter, wherein a flow field seeded with small particles is illuminated by a collimated monochromatic sheet of laser light.

The Adrian, et al. Patent, U.S. Pat. No. 4,729,109, describes a method and apparatus for measuring the displacement of particle images through multiple exposure velocimetry with a pulsed laser.

U.S. Pat. No. 5,333,044 discloses a fluorescent image tracking velocimeter that tracks the displacement of fluorescent particles in a fluid over time.

The Cha patent, U.S. Pat. No. 5,532,814, discloses holographic diffraction image velocimetry for three-dimensional, three component particle fields or solid objects.

There are other patents that disclose arrangements which involve the positioning of video cameras at differing angular positions relative to an object such as U.S. Pat. Nos. 5,396,331; 5,110,204; 4,709,580; and 4,337,049. Other laser techniques for determining particle velocimetry are described in U.S. Pat. Nos. 4,988,191 and 5,011,278.

There still exists a need for an apparatus and method that provides state of the art, full-field, three-dimensional flow analysis for any optically transparent fluid seeded with tracer particles regardless of size. Preferably, such a method would not require the use of lasers or other complex equipment with highly specialized optics. Lasers can cause safety concerns as well as limit the type of application. Also, there exists a need for an apparatus and method which would use off-the-shelf hardware that is easily adapted to most three-dimensional applications. It should provide an accuracy to within approximately 2% of full-field which is more accurate than any other three-dimensional system to date. It is desirable to have a modular design with each module being a fully functional stand-alone technique.

DISCLOSURE OF INVENTION

It is an object of the present invention to provide a system for measuring three-dimensional velocities at a plurality of points in a fluid.

It is a further object of the present invention to provide a method for measuring three-dimensional velocities at a plurality of points in a fluid.

It is a further object of the present invention to provide a system for collecting quantitatively, three-dimensional flow data from an optically transparent fluid having tracer particles.

It is a further object of the present invention to provide a state of the art, full-field, three-dimensional flow analysis system for any transparent fluid seeded with tracer particles regardless of size.

It is a further object of the present invention to provide a stereo imaging velocimeter which does not require the use of lasers or complex equipment such as highly specialized optics, but rather uses off-the-shelf hardware so that it may be easily adapted to most three-dimensional applications.

It is a further object of the present invention to provide a stereo imaging velocimeter with an accuracy to within approximately 2% of full-field.

It is a further object of the present invention to provide a stereo imaging velocimeter with a modular design with each module being a fully functional stand-alone technique.

It is a further object of the present invention to provide a stereo imaging velocimetry system that provides three-dimensional, full-field, quantitative and qualitative vectors from two or more cameras aligned approximately perpendicular with respect to each other.

It is a further object of the present invention to provide a stereo imaging velocimetry system which does not require highly specialized optics.

It is a further object of the present invention to provide a camera calibration method that is sturdy, efficient, easily implemented, and highly accurate.

Further objects of the present invention will be made apparent in the following Best Modes for Carrying Out Invention and the appended claims.

The foregoing objects are accomplished in a preferred embodiment of the invention by a system that measures three-dimensional velocities at a plurality of points in a fluid seeded with tracer particles. At least two cameras are positioned to view the fluid seeded with tracer particles. The two cameras are positioned approximately perpendicular to one another to provide two, two-dimensional views of the tracer particles seeded in the fluid. Signal processing means connected to the cameras receive and record the two-dimensional views. Centroid determining means in communication with the signal processing means accurately locates a centroid of each tracer particle in a frame and establishes coordinates therefor. Overlapping tracer particle clusters are decomposed into constituent centroids with means for decomposing overlapping tracing particle clusters. The tracer particle tracks are determined for a correspondence between individual tracer particles over time and across the orthogonal views so that tracking is accomplished in two dimensions. Stereo matching means determines which individual tracer particle images from synchronized images represent identical tracer particles for calculating three-dimensional coordinates from the two-dimensional coordinates as a function of time and distance. The present invention collects quantitative, three-dimensional flow data from the optically transparent fluid having tracer particles to thereby provide three-dimensional velocities at a plurality of points.

The preferred method of the present invention measures three-dimensional velocities at a plurality of points in the fluid. At least two cameras are positioned to view a fluid with the cameras being approximately perpendicular to one another. A coordinate system for each camera is defined based on a world coordinate system. A two-dimensional view of the fluid seeded with the tracer particles is recorded for each camera. Centroid coordinates are determined from the two-dimensional images of the tracer particles, and tracer particle tracks are determined as viewed by each camera based upon the centroid coordinates. The two-dimensional tracer particle tracks between the camera views are stereo matched for finding three-dimensional locations of the tracer particles as a function of time and measuring velocities thereof. A consistency check is performed on a calculated velocity field and any tracer particle tracks which are not in agreement with neighboring tracer particle tracks are discarded. Additionally, the method decomposes overlapping tracer particle clusters into constituent centroids. In a preferred form, the method uses major axis length and circumference for recognizing overlapping tracer particles when decomposing overlapping tracer particles. Preferably, the method of the present invention employs a four frame sequence for tracing tracer particles which advantageously reduces computational complexity by at least an order of magnitude. The method of the present invention provides a camera calibration approach that calibrates each camera by imaging a calibration target plane containing calibration points. Camera calibration coefficients are determined to correct for camera aberrations.

BRIEF DESCRIPTION OF DRAWINGS

FIG. 2A is a schematic representation of the fluid volume illustrating the world coordinate system defined so that its origin is at or near the center of the imaged fluid volume.

FIG. 2B is a schematic illustration of the imaged plane of the second camera 20 with its center corresponding to the center of the pixel array.

FIG. 2C is a schematic representation of the image plane of the first camera 18 showing its coordinate system defined with the center corresponding to the center of the pixel array.

BEST MODES FOR CARRYING OUT INVENTION

Figure 1A:
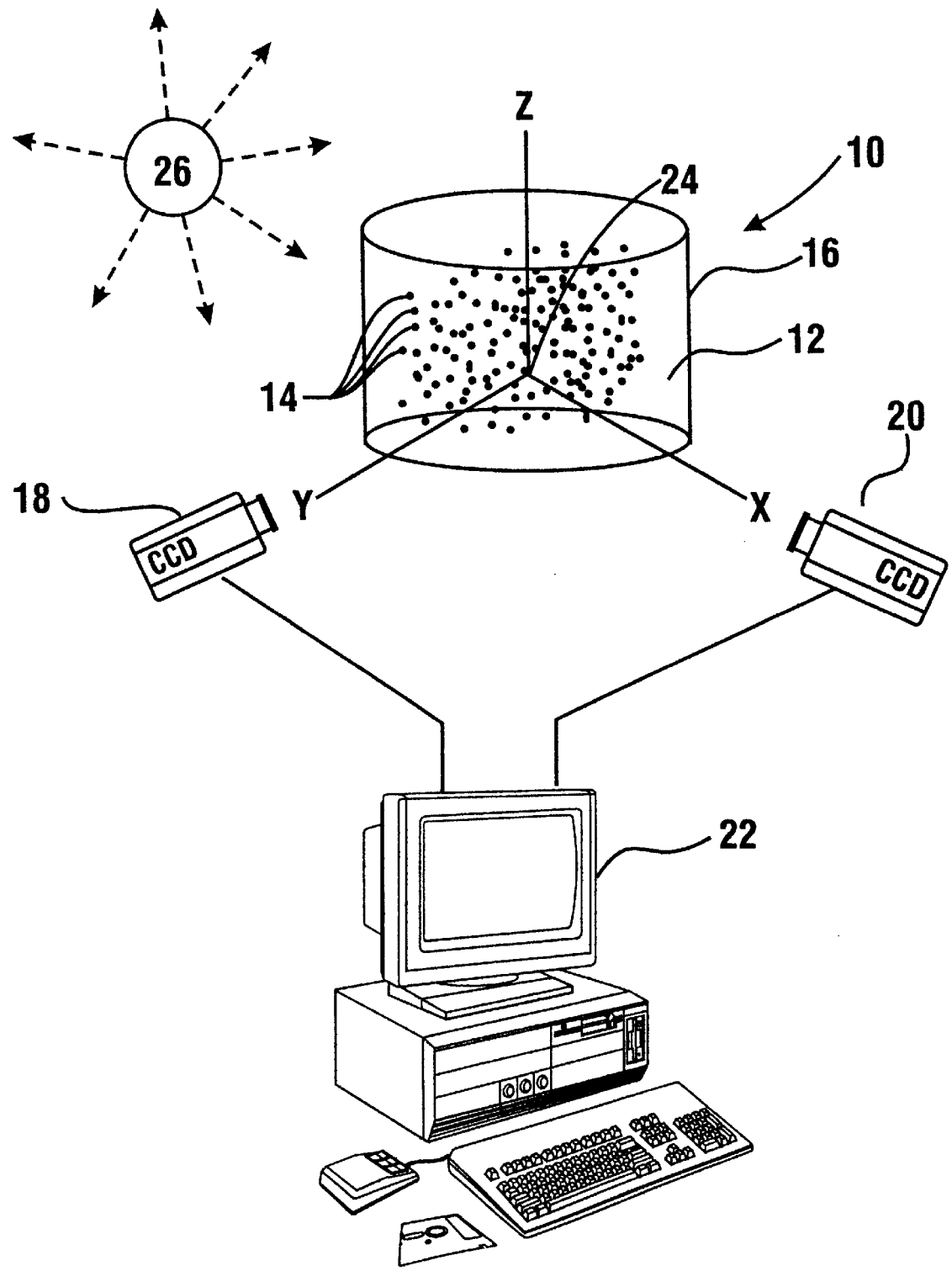
FIG. 1A is a schematic illustration of the system in accordance with the present invention imaging a fluid volume seeded with tracer particles showing X, Y, Z coordinates.
Figure 1B:
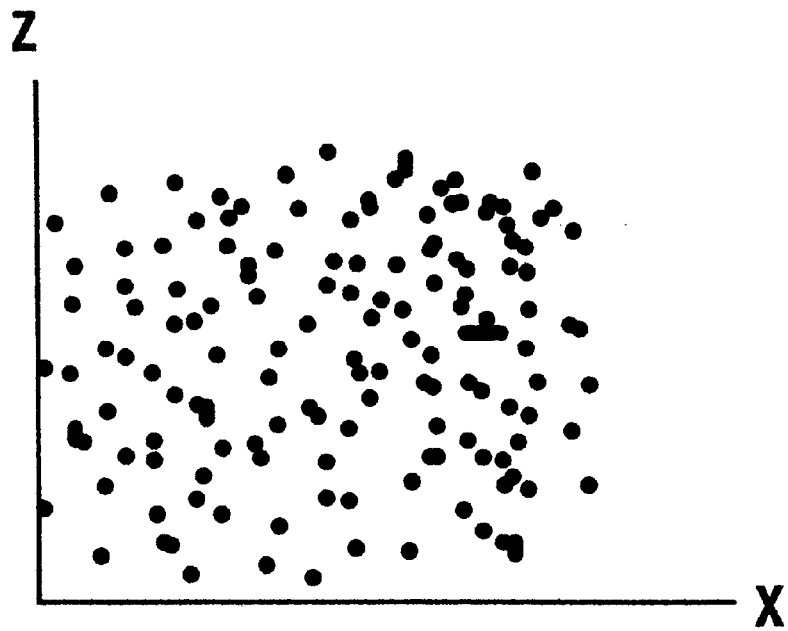
FIG. 1B is a view of the image recorded by the first camera 18 referenced as the Y, Z dimension.
Figure 1C:
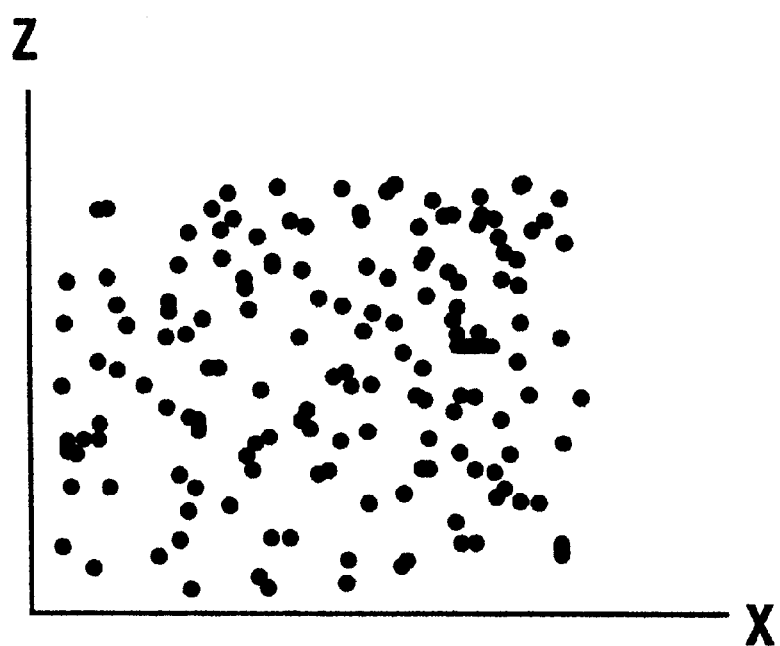
FIG. 1C is a view of the image recorded by the second camera 20 referenced as the X, Z dimension.

Referring now to the drawings where like numerals designate like or similar features throughout the several views, and first to FIGS. 1A through 1C, there is shown a system generally designated 10 for measuring three-dimensional velocities at a plurality of points in an optically transparent fluid 12 having tracer particles 14 seeded therein. Fluid 12 with tracer particles 14 are contained within a fluid volume 16 such as a conduit or chamber. It should be understood that the present invention finds applicability to a fluid or fluid stream, for example, a fluid flowing through a conduit or a fluid having motion within a set fluid volume. A first or left camera 18 which is preferably a charge coupled device (CCD) is positioned so that it is approximately perpendicular to a second or right camera 20 which is also preferably a CCD camera. Cameras 18, 20 are electronically connected to computer 22. The first camera 18 images the Y-Z coordinate plane as illustrated in FIG. 1B. The second camera 20 images the X-Z coordinate plane as illustrated in FIG. 1C. This geometry was selected because it maximizes the accuracy of depth perception, but it also complicates the stereo matching or correspondence problem This is more than compensated for by the increased accuracy in depth measurement. The coordinate system of each camera is defined to be nearly parallel to and approximately centered on the world coordinate system which is defined with its origin at or near the center 24 of the fluid volume 16. Fluid 12, which may be gas or liquid, is an optically transparent fluid which is seeded with a selected density of tracer particles 14. The type of tracer particles used depends on the flow media and the measurement conditions such that the seed material does not alter the flow field conditions being measured. Some typical tracer particles may include but are not limited to alumina oxide, latex particles, polystyrene, microspheres, and the like.

The present invention employs conventional off-the-shelf lighting from a light source 26 to provide illumination for cameras 18, 20. System 10 also referred to as a stereo imaging velocimeter provides a full-field, quantitative, three-dimensional map of any optically transparent fluid which can be seeded with tracer particles. Through stereo imaging velocimetry, system 10 permits the collection of quantitative, three-dimensional flow data and provides a means to accurately measure three-dimensional velocities simultaneously at many points.

As the tracer particles 14 move with the fluid 12, cameras 18, 20 record two, two-dimensional views simultaneously. These images are stored in real-time with signal processing or image analysis means such as laser disk recorders that may be integrated within the computer system 22, or be separate stand-alone systems (not shown) in electronic communication. After an experiment or test is complete, images are read back from the laser disks. Computer 22 performs any necessary image preprocessing such as thresholding and image subtraction. The images are then scanned to find the particle location. The two-dimensional images of the tracer particles are reduced to sets of centroid coordinates which are stored in ASCII files. Working with sets of four time steps, the tracer particle 14 tracks as viewed by each camera 18, 20 are determined. Computer 22 provides means for stereo matching the tracks between views to find the three-dimensional locations of the tracer particles 14 as a function of time. A consistency check is performed on the calculated velocity field to discard any tracks which may be in significant disagreement with neighboring tracks.

The present invention advantageously employs standard NTSC (National Television System Committee) signals in order to be compatible with most image processing hardware/software devices. An NTSC limitation is a maximum framing rate of 30 Hz. This coupled with the field of view determines the maximum velocity which the stereo imaging velocimetry system can measure. In general, if a particle moves more than 5–10% of the field of view between frames, the tracking module may fail. For example, with an experimental volume 5 cm on a side, this amounts to a maximum velocity of 7.5–15.0 cm/sec. Another consideration is the cameras themselves.

CCD cameras operate with an every-other-line scan pattern: the 1/30th second time interval between frames is divided into two 1/60th second sub-intervals. The first sub-interval is used to scan in the odd pixel lines. The second sub-interval is used to scan in the even pixel rows. This dual scan pattern can be used to double the framing rate at the expense of halving the vertical resolution: at time equals 1/60 sec, the odd lines are read to define particle positions, and at time equals 2/60 sec, the even lines are read to find their new positions. If the sensor field is being regarded as a whole, significant blurring effects from the CCD scan pattern occur when the particles move a pixel or more in 1/60 sec. In the example above (e.g. a cube of 5 cm), this corresponds to a velocity of 3 mm/sec.

While this problem can be circumvented by using CID (Charge Injection Imaging Device) cameras which do not artificially divide the sensor field, and have a true framing rate of 30 Hz, CCD cameras provide a relatively low cost with ease of use and flexibility. Where higher speeds are necessary, there are higher frame rate cameras available. The term "cameras" as used herein is intended to encompass not only CCD cameras or even CID cameras but any imaging means applicable for obtaining three-dimensional vectors such as sonar, radar, thermal imagery, or other two-dimensional imaging means for providing data sets.

The stereo imaging velocimetry of the present invention basically consists of five main phases: camera calibration which is the ability to accurately represent image coordinates in world or absolute coordinates; centroid determination which is the ability to determine the geometrical center of an object; overlap decomposition which is the ability to decompose individual particle clusters into constituent centroids; stereo matching which is the ability to accurately match left and right camera views; and particle tracking which is the ability to accurately track a particle's velocity over time. As employed herein, the terms world coordinate system and absolute coordinate system mean the same thing, i.e., a true three dimension coordinate system.

Since camera calibration is one of the most important aspects of any computer vision or image processing experiment, the present invention provides a novel camera calibration technique that is robust, efficient, easily implemented, and highly accurate. The error associated with camera calibration is the limiting factor in any experiment using image analysis since accuracy is always limited by calibration error. Camera calibration is critical because it permits the jump from qualitative to quantitative data. Camera/lens systems have nonlinearities which may be minimized, but not avoided altogether. These nonlinearities are detrimental to stereo imaging velocimetry because they shift data an unknown amount, changing both the relative and absolute positions of the images recorded by the camera. The fluid volumes themselves, for example, transparent tanks and liquids, can add further distortions through curved geometries and index of refraction changes.

To make quantitative measurements of the motion of the tracer particles 14 suspended in the fluid 12, an absolute coordinate system is used as a reference to evaluate their positions. This coordinate system is referred to as the world coordinate system and defined such that its origin is at or near the center 24 of the imaged fluid volume. This is where the principal optical axes of the two cameras 18, 20 have their point of nearest intersection. Also, it is preferable that the tracer particles 14 be neutrally buoyant to permit accurate flow tracking.

Next, referring to FIGS. 2A–2C, each camera 18, 20 has its own coordinate system being defined as tied to its image plane. FIG. 2C illustrates the pixel array 32 for the first camera 18 with coordinates $+X_1$, $+Y_1$, $+Z_1$. FIG. 2B illustrates the pixel array 34 for the second camera 20 with its coordinates $+Z_2$, $+X_2$, $+Y_2$. The center 24 corresponds to the center of the pixel array 32, 34 for the first and second cameras, respectively. The X and the Y axes extend along the rows and columns of the array 32, 34 and the Z axis points along the optical axis of the lens system as shown in FIGS. 2B and 2C.

Since the two cameras 18, 20 are oriented imprecisely with respect to the world coordinate system $X_w$, $Y_w$, $Z_w$, the relationship between the three coordinate systems needs to be determined in order to correlate the two-dimensional camera determined measurements to real, three-dimensional positions. Additionally, optical aberrations from the lenses as well as from the measurement technique itself, such as index of refraction mismatches, can distort the measurements if not properly taken into account. All of these corrections together are meant to be included in the term "camera calibration". As mentioned earlier, it is to be understood that while conventional light optical cameras 18, 20 are described in the present invention, that stereo imaging velocimetry is a general technique which could be applied to obtain three-dimensional vectors from sonar, radar, thermal imagery, or other two-dimensional data sets.

Figure 3:
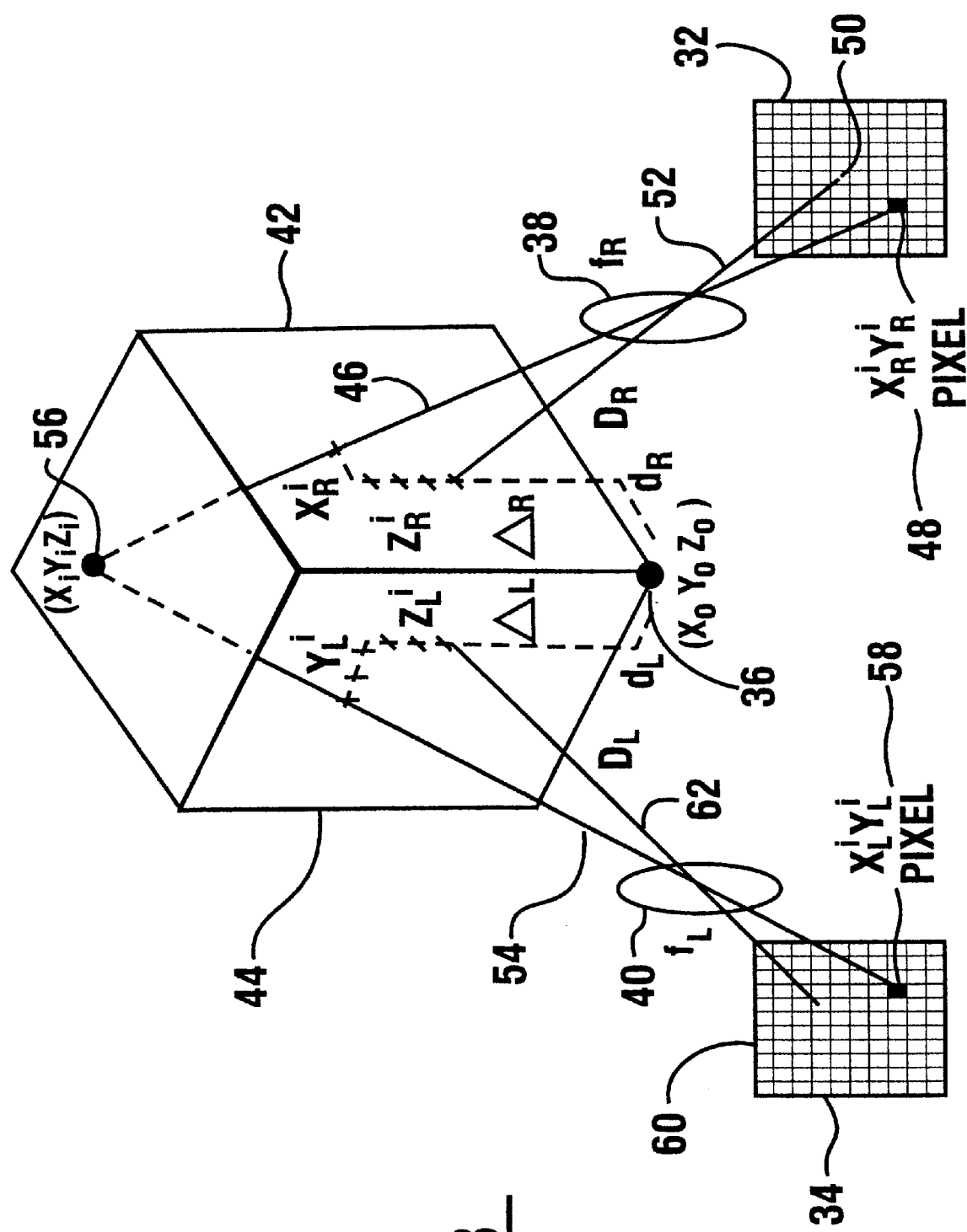
FIG. 3 is a schematic representation of the camera calibration geometry illustrating the right and left camera views.

Referring next to FIG. 3, there is shown the camera calibration geometry according to the present invention. The origin of the absolute coordinate system 36 ($x_0$, $y_0$, $z_0$) is placed such that it is in the lower left hand corner of the fluid flow chamber 16 when viewed by the second or right camera 20 (the lens of camera 20 being schematically depicted as 38) and in the lower right hand corner of the chamber when viewed by the first or left camera 18 (the lens of the left camera 18 being schematically depicted as 40). FIG. 3 shows the right window coordinates 42 and the left window coordinates 44 representing the images planes of the fluid chamber. This geometry defines the right and left camera views in two, two-dimensional views. $x_i$, $y_i$, $z_i$ are the absolute x, y, z coordinates of particle i with respect to the origin 36.

A ray of light 46 leaves a tracer particle $x_i$, $y_i$, $z_i$ and strikes the right camera pixel array 32 at location $x^i{}_R, Z^i{}_R$ designated 48 with respect to the center of the array 50 which is taken to be on the symmetry axis 52 of the camera lens 38. The effective focal length of the right camera being represented as $f_R$. The effective distance between the right camera and the face of the chamber being designated $D_R$. The horizontal distance of the right camera axis from the origin being designated $d_R$. The vertical distance of the right camera axis 52 from the origin is designated $\Delta_R$. $C_R$ represents the camera dependent constant with the units in mm/pixel. $x^i{}_R, Z^i{}_R$ represents the window coordinates of particle i on the face 42 of the chamber from the right camera's 20 perspective. The left camera's 18 perspective is analogous with the $_R$ being replaced with a $_L$.

Another ray of light 54 leaves particle i 56 and strikes the left CCD camera 18 pixel array 34 at the pixel location $y^i{}_L, Z^i{}_L$ designated 58 with respect to the center of the array 60 which is taken to be on the symmetry axis 62 of the camera lens 40. $D_R$ and $D_L$ are the effective distances of the cameras from the right 42 and left 44 faces, respectively, of the tracer particle chamber. $f_R$ and $f_L$ are the focal lengths of the right 20 and left 18 cameras, respectively. The left camera axis is a distance $\Delta_L - \Delta_R$ higher than the right camera axis 52 and intersects the right face of the particle chamber a distance $d_L$ from the edge with respect to the left face 44. The ray 46 going from tracer particle 56 to the right camera lens 38 crosses the right face 42 of the particle chamber a distance $Z_R{}^i$ above and $X_R{}^i$ to the right of the axis 52 of the right camera 20. The ray 54 going from particle i to the left camera lens 40 crosses the left face 44 of the particle chamber a distance $Z_L{}^i$ above and $Y_L{}^i$ to the left of the axis 62 of the left camera.

During calibration, one knows the absolute coordinates ($x_i$, $y_i$, $z_i$) and pixel readouts ($x^i{}_R, Z^i{}_R$)($y^i{}_L, z^i{}_L$) of predetermined calibration points. $f_L$, $D_L$, $\Delta_L$, $d_L$, $f_R$, $D_R$, $\Delta_R$, and $d_R$ are determined by least squares data fitting so that during camera operation after the calibration procedure is completed, the absolute coordinate $x_j$, $y_j$, $z_j$, of a tracer particle entrained in the flow are determined with only its pixel positions ($x^j{}_R, Z^j{}_R$)($y^j{}_L, Z^j{}_L$) on the cameras.

The preferred approach is to determine the camera calibration parameters reliably by imaging a calibration target plane containing calibration points. The pixel positions of the image of the reference mark or calibration point will always have some random error (±) associated with them There are several variables that need to be determined such as how many reference points to make on the calibration target plane, how large the calibration target plane should be, and where the calibration target plane should be placed inside the fluid volume chamber. This insures that the error (±) associated with the pixel positions would be minimal.

The camera calibration approach of the present invention can be divided into the following nine steps:

Step 1: Choose the positions of a number (N) reference points in space (absolute coordinates);

Step 2: Use a physical model to determine the exact pixel locations of these N reference points;

Step 3: Choose realistic values of all the camera parameters to input into the physical model;

Step 4: Add a random amount of error (±L) to the calculated pixel positions in order to obtain "pseudo experimental pixel values";

Step 5: Input the absolute coordinates and the pseudo experimental pixel values of the N reference points into a least squares fitting method in order to obtain the "pseudo experimental camera parameters";

Step 6: Compare the pseudo experimental camera parameters with their predetermined values from Step 3;

Step 7: Add new random errors (±) to the calculated pixel positions, and redo Steps 5 and 6;

Step 8: Change the number N and redo Steps 1–7;

Step 9: Change the absolute locations of the reference points, and redo Steps 1–8.

The data generated from these calibration target points is applied to a least squares fitting procedure in order to determine which set of calibration points best fit the camera calibration model of an experimental fluid chamber 16. The best fit is used to obtain camera calibration coefficients for correction of camera aberrations when conducting measurements. A comparison of the results from the calibration approximated points to real world (absolute) coordinates provides camera calibration error.

The left camera view (YZ view) and the right camera view (XZ view) are calibrated separately, and then combined to produce the three-dimensional (XYZ) calibration routine. The technique is based on using several, for example, three, parallel calibration planes placed inside a volume or chamber so that both cameras can view the calibration points simultaneously. One selects the positions of a number of calibration points in a volume (absolute coordinates-x, y, z) and uses a physical model to determine the exact pixel locations of the calibration points. The absolute points and pixel locations are input into a least squares fitting algorithm to obtain the experimental camera parameters.

When analyzing a theoretical model, a camera calibration accuracy of less than 1.30 pixels was achieved. When analyzing a two-dimensional experimental model truncated to nine terms, a camera calibration accuracy was achieved of less than 2.47 pixels for the left camera view and 2.29 pixels for the right camera view. When combining the left and right views to produce one three-dimensional calibration, an accuracy was achieved of less than 3.43 pixels. The foregoing camera calculations were performed on a 486 microprocessor based computer and the typical calibration time from start to finish usually takes less than ten minutes. The calibration tests conducted on volumes of 0.3 inches, 1 inch, and 3 feet for industrial applications achieved similar calibration results. The results show that the camera calibration routine is mathematically sound and experimentally verified as well as being easily implemented into any existing three-dimensional experiment to produce accurate, quantitative information.

After establishing an accurate camera calibration method, the largest source of error in the stereo imaging velocimetry system is the centroid determination. Contributors to this error are data acquisition hardware, spatial and gray level quantization, and overlapping particles. It is important that the centroid of each particle be accurately located in every frame, because the coordinates of the centroid will be used for stereo matching and particle tracking. Hence, any miscalculations of centroid location will be a direct cause of miscalculation of two-dimensional velocities at the least, and may lead to incorrect matches when performing the stereo matching which will lead to large errors in the third dimension. The centroid algorithm of the present invention accurately traces the edges of a particular multi-pixel blob and identifies its centroid in order to predict the trajectory of the particle as a function of time in stereo imaging velocimetry experiments. The particles in the experiments are expected to be three to five pixels in diameter. The size is important, because with these diameters the particles are big enough to have a many-pixel boundary. Additionally, the particles are small enough that quantization errors around their edges can have a significant effect; the locations of their centroids can be determined accurately only by using the intensity information which is quantized. The present invention is concerned with both an accurate edge finding routine and in preserving the intensity profiles of the tracer particles.

The edge finding is based on using two components of the image, its gray level intensity value, and its location in the 512 (i=columns)×480 (j=rows) viewable image. It is based on the Initial Point Algorithm (IP Algorithm) which looks for the first point of a contour and the T Algorithm, which is used to trace the contour of a particle as taught by Rafael C. Gonzalez and Paul Wintz, in Digital Image Processing, Second Edition, Addison-Wesley Publishing Co., pgs. 275 to 287, 1987. Using the Left-most-looking rule (LML), one always looks first at the element to the left relative to the direction that it is going. This centroid is based on using the standard center of mass equation which correlates to an intensity-weighted center of mass equation in discrete form. In the following equation, $$R_{cm} = \frac{\sum_{j=jmin}^{jmax} \sum_{i=imin}^{imax} [i \cdot f(j,i)\hat{v}_x + j \cdot f(j,i)\hat{v}_y]}{\sum_{j=jmin}^{jmax} \sum_{i=imin}^{imax} f(i,i)} \quad (1)$$

where:

$R_{cm}$ is the term used for the center of mass i represents the column position j represents the row position $V_x$ represents the row vector $V_y$ represents a column vector Another problem in solving stereo imaging velocimetry is the overlapping particle problem. A large source of error in solving this problem is centroid error. Other contributing factors to this error are the data acquisition hardware, spatial quantization, and gray-level quantization. Overlapping particles are a function of the degree to which the fluid flow is seeded, i.e. data density. They cause inaccurate centroid locations if the objects (blobs) are not properly identified as consisting of more than one particle. This improper identification not only loses particles, but the blob's centroid is not accurate for any of its constituent particles. Hence, any miscalculations of centroid locations will be a direct miscalculation of two dimensional velocities at the least, and may lead to incorrect matches when performing stereo matching, which will lead to large errors when three-dimensional analysis is performed.

It is known that overlapping particles induce errors on the centroid location by as much as the particle radius, which increases the overall error of the velocity vectors.

Overlapping of the multi-pixel blobs (imaged particles) occurs when particles which are close to the camera partially obscure the ones which are further away. Particle overlaps must be resolved for two reasons:

1. To preserve the total number of particles; and
2. Unless the region can be properly decomposed into its constituents, the centroid error of the blob can be as large as the particle radius.

Induced errors of this magnitude would effectively negate the accuracy of any stand-alone centroid finding algorithm Thus, in stereo imaging velocimetry image processing, it is necessary to integrate centroid finding in particle overlap decomposition. This generally occurs in a logical, sequential manner.

Overlapping particles can be resolved by the human eye using four primary features: major axis length of the bounding ellipse, minor axis length of the bounding ellipse, circumference, and the indention at the point of overlap. It has been shown that the indention at the point of overlap could not be consistently measured and that the minor axis length provided little information. The system of the present invention uses only the major axis length and the circumference to recognize overlapping particles. Each particle-blob region must first be located and its centroid extracted before particle overlap decomposition can be performed.

In general, the larger the circumference and the major axis length, the higher the probability that the blob region is composed of multiple overlapping particles. This provides the basis for the overlapping particle algorithm of the present invention.

At reasonable seed densities in a constant volume, it is statistically improbable that a blob region will be composed of more than three overlapping particles. This statement is based on many synthetic and real images to obtain data required for the empirically derived equations which describe these functional relationships. Thus, the probability relationships between the major axis length and the circumference were determined for up to three overlapping particles. Both the major axis of the bounding ellipse and the circumference vary linearly with respect to the particle radius. This fact is significant because the probability relationships can be "learned" for one size of particle and be transposed to other experiments through functional normalization. The probability relationships are actually learned for the major axis and circumference normalized by the particle radius. The probability that a blob region is a single, double, and triple particle region can be obtained following the extraction of the feature vector, (the major axis length, circumference). This is accomplished by entering the features into the empirically derived probability equations described below. In all equations, x is the value of the appropriate feature.

$$P(\text{single}) = 1 - \frac{1}{1 - e^{-\frac{x+q}{t}}} \quad (2)$$

$$P(\text{triple}) = 1 - \frac{1}{1 - e^{\frac{x+b}{c}}} \quad (3)$$

$$P(\text{double}) = 1 - P(\text{single}) - P(\text{triple}) \quad (4)$$

Circumference q=−8.5 t=−0.16*q b=−16.5 c=−t

Major Axis q=−4.0 t=−0.14*q b=−7.3 c=−t

Parameters q, t, b and c are shown above for the major axis length and circumference as defined by the test images descried herein. These values were determined for 168 micron particles at a distance of 27.5 centimeters (cm) from lens system to the middle of the imaged volume. Thus, the probability curves can be determined for any experimental setup by normalizing these functions with respect to these values. c and t as a function of other parameters, remain the same and q and b are defined as follows:

$$q = q * \frac{\text{Particle size}}{168 \text{ microns}} * \frac{27.5 \text{ cm}}{\text{Camera Distance}} \quad (5)$$

$$b = b * \frac{\text{Particle size}}{168 \text{ microns}} * \frac{27.5 \text{ cm}}{\text{Camera Distance}} \quad (6)$$

This algorithm has been tested using synthetic, simulated and real data. The hardware used to develop and implement the Stereo Imaging Velocimetry image processing includes an IBM® Compatible Pentium® computer interfaced with a Recognition Technology Incorporated (RTI) image analysis subsystem and a SONY® 3-Chip Charge Coupled Device (CCD) video cameras. The images examined were 512×512 pixels with 512×480 pixels viewable and accessible using the RTI. The RTI system is a complete image analysis system that enables a user to apply an assortment of standard and advanced image analysis techniques. Suitable software for image analysis includes but is not limited to Microsoft® C (version 5.10) and Borland® C/C++ (version 3.1). The accuracy of the algorithm is determined by the relative error between a known shape and center compared with the shape and center calculated by the algorithm. The following definitions explain terms used throughout this application.

Computer-Generated Data—(Image Analysis System to Computer). Data is generated by the computer and analyzed by the image analysis system. When using synthetic data, the exact locations of all particle edges and their centroids are known. This data is used as an initial test to validate the algorithm The results are given in Table 1.

TABLE 1

COMPUTER-GENERATED Data (Average over 5 test runs)

| Number of Random Particles | Yield Without Overlap Decomposition | | Yield With Overlap Decomposition | |
|---|---|---|---|---|
| 50 | 47.6 | (95.2%) | 49.8 | (99.6%) |
| 100 | 93.0 | (93.0%) | 99.6 | (99.6%) |
| 150 | 134.0 | (89.3%) | 148.8 | (99.2%) |
| 180 | 156.4 | (86.9%) | 178.2 | (99.0%) |

Simulated Data—(Test Grid to Camera to Image Analysis System to Computer). Data is generated by using a print-out of the synthetic data imaged by a camera, routed to the Recognition Technology Incorporated (RTI) image analysis system, then analyzed by a computer. The simulated data is used in order to generate the error associated with the image analysis set-up. This error will vary from set-up to set-up based on the quality of equipment being used. The results are given in Table 2.

TABLE 2

SIMULATED Data (Average over 5 test runs)

| Number of Random Particles | Yield Without Overlap Decomposition | | Yield With Overlap Decomposition | |
|---|---|---|---|---|
| 50 | 47.6 | (95.2%) | 49.6 | (99.2%) |
| 100 | 92.2 | (92.2%) | 98.4 | (98.4%) |
| 150 | 135.0 | (90.0%) | 148.2 | (98.8%) |
| 180 | 155.8 | (86.6%) | 177.6 | (98.7%) |

Real Data—(Experiment to Camera to Image Analysis System to Computer). Data from a real experiment is imaged by the camera, routed to the image analysis system, then analyzed by computer. A 3"×3" cylindrical chamber was used and filled with water and seed particles with densities of 100, 150, 200, 250 and 300 particles. The results are given in Table 3. The size of the particles in Table 3 are 200 microns.

TABLE 3

REAL Data (Average over 5 test runs)

| Number of Random Particles | Yield With Overlap Decomposition | |
|---|---|---|
| 100 | 94.4 | (94.4%) |
| 150 | 140.0 | (93.3%) |
| 200 | 188.6 | (94.3%) |
| 250 | 236.8 | (94.6%) |
| 300 | 270.8 | (90.3%) |

From the orthogonal camera views, two sequences of images are obtained of the fluid chamber. Each sequence has a period of ⅓₀th of a second. Having performed the prior steps of calibration, preprocessing, centroid determination and particle overlap decomposition, it remains to determine the correspondence between individual particle images across time and across orthogonal views.

One can track in two dimensions and then stereo match tracks from left and right camera images to obtain three-dimensions. Alternatively, one can stereo match the particles beforehand and track directly in three dimensions. The present invention uses the former approach because it reduces the problem search-complexity by one dimension while providing a step subsequent to the tracking phase which serves to prune invalid tracks.

Each image holds many particle images. Each particle image, in simplified terms, may be specified by the doublet as follows:

$$(P_c(k,t), f_0+t) = ((x_c(k,t), y_c(k,t), f_0+t) \quad (7)$$

Where $(x_c(k,t), y_c(k,t))$ = particle centroid for particle image k in frame $f_0+t$ $f_0+t$ = image frame sequence number ($f_0$ is the starting time)

As mentioned before, images are taken at a uniform time interval at ⅓₀ second intervals. A track is then defined as a sequence of four of the doublets in Equation 7 according to the following formula:

$$\{(P_c(k_1,1), f_0+1), (P_c(k_2,2), f_0+2), (P_c(k_3,3), f_0+3), (P_c(k_4,4), f_0+4)\} \quad (8)$$

It takes three doublets to define a constant acceleration, while the fourth frame is retained in order to provide a check on the validity of an assumption of constant acceleration. Others have taught of tracking particles in a five frame sequence to enforce a more rigorous standard of track smoothness. However, longer sequences exclude more tracks in turbulent flow. They also increase the search space in an exponential manner. For these reasons, the present invention elects to use four frames. In order to find the correct tracks, the present invention has adopted a two-step process. First, the problem is initialized by selecting all possible tracks which conform to several key limiting constraints. Second, a global-optimization scheme is utilized to find the best set of tracks.

During the first phase, track initialization, an unrestricted search of hundreds of particle images over four frames would be inefficient. Fortunately, two limiting assumptions are made about track characteristics. The first assumption is to assume a maximum velocity constraint which implies that a particle cannot travel beyond a fixed radius between successive image frames. The second assumption is to assume a maximum acceleration constraint which further limits the number of acceptable choices in the third and fourth frames. The process of selecting particle image candidates for potential tracks is illustrated in FIG. 4.

Figure 4:
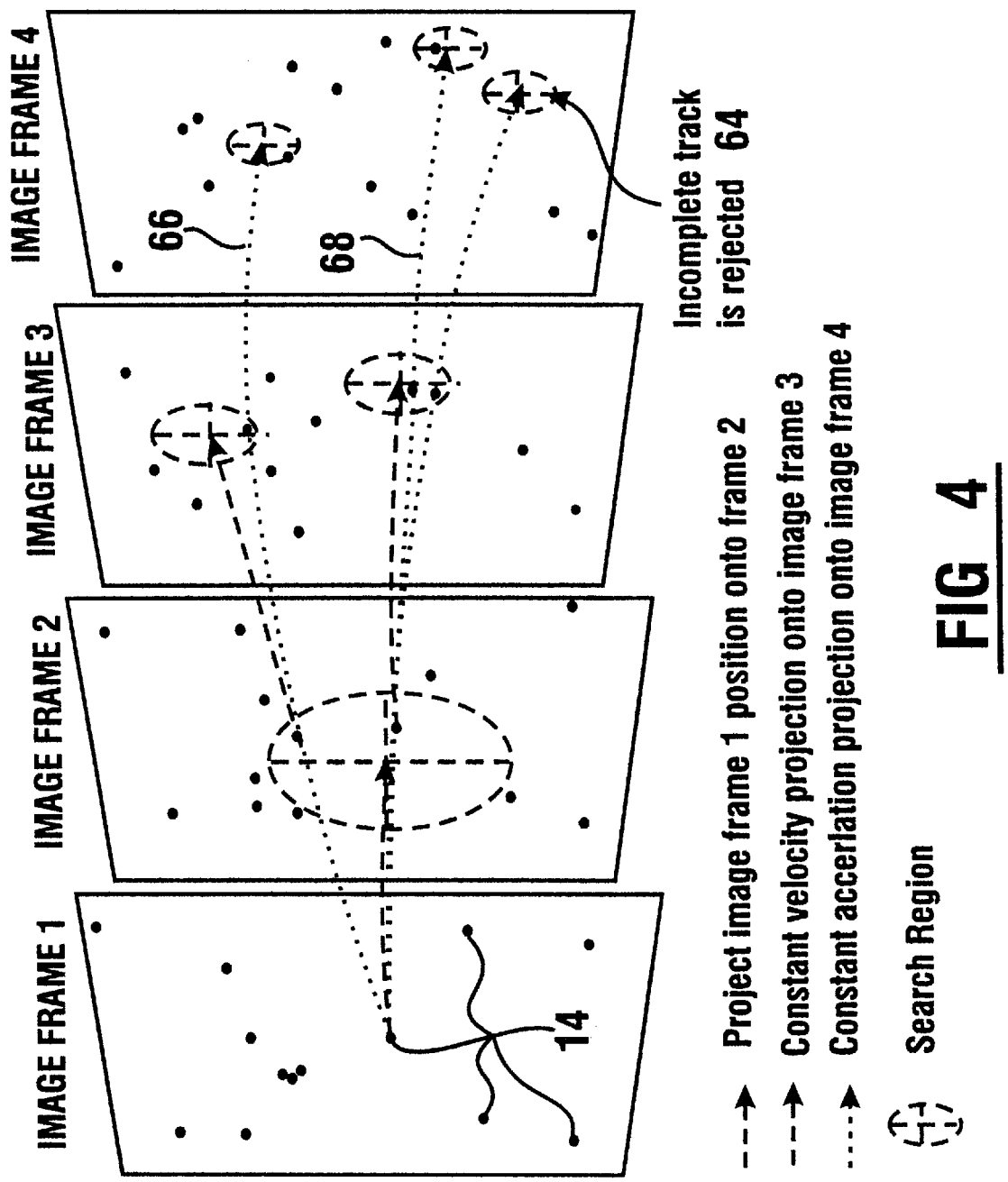
FIG. 4 is an illustration of four frame images illustrating the manner in which potentially valid tracks are identified.

FIG. 4 illustrates an example of the manner in which potentially valid tracks are identified. An empty search region 64 terminates a track fragment. In this example, two valid tracks 66, 68 are identified in image frame four. One of these track options will ultimately be favored over the other as a result of optimization.

Having found all possible acceptable tracks, it is necessary to select from among them to find the correct set. To achieve this, a technique is implemented of P. P. C. Yip and Y. H. Pao, "Combinatorial Neural Networks With Use of Guided Evolutionary Simulated Annealing", IEEE Transactions on Neural Networks, accepted for publication (1994) was developed which they referred to as "Guided Evolutionary Simulated Annealing" neural net to perform global optimization. Guided Evolutionary Simulating Annealing Optimization Algorithm (GESA) is a stochastic search method which learns to ignore less promising configurations in favor of better ones. This allows a problem to converge in something less than exponential time. The present invention provides numerous advantages to other approaches. First, the approach according to the present invention restricts the search space to complete valid tracks identified during the previously mentioned set-up phase. Second, the evolutionary net with simulated annealing is a stochastic search method which is less susceptible to being stuck in local minima. Third, an interventionist strategy was adopted whereby randomly selected tracks would not be laid down until any obstructing tracks were moved out of the way (or deselected altogether). This step, a simple acknowledgment of the fact that a valid configuration can never overlap, minimizes or eliminates high intermediate energy barriers. Fourth, great effort was expended to find an optimal definition of a valid track. Fifth, as mentioned previously, the number of images per time sequence per track was reduced from five to four, reducing computational complexity by an order of magnitude.

Terrain following optimization algorithms such as back-propagation of error, tend to get stuck in local energy minima. Stochastic search methods, such as the one described above, are not trapped as easily and so are more robust.

The final step in the method of the present invention is to stereo match. Stereo matching consists of determining which of the many particles in a pair of synchronized images from the two cameras represent the same particle photograph from different perspectives. The assumption is that all the particles will be identical in appearance. The only unique information then is the z coordinate of each particle. The tracks of the particles can either be determined simultaneously with the matching, or one can choose to do the tasks one at a time, first tracking and then stereo-matching, or vice versa. The advantage of first tracking is that the z coordinate may be used as a basis for matching, plus there is a time history of the z coordinate.

Figure 5:
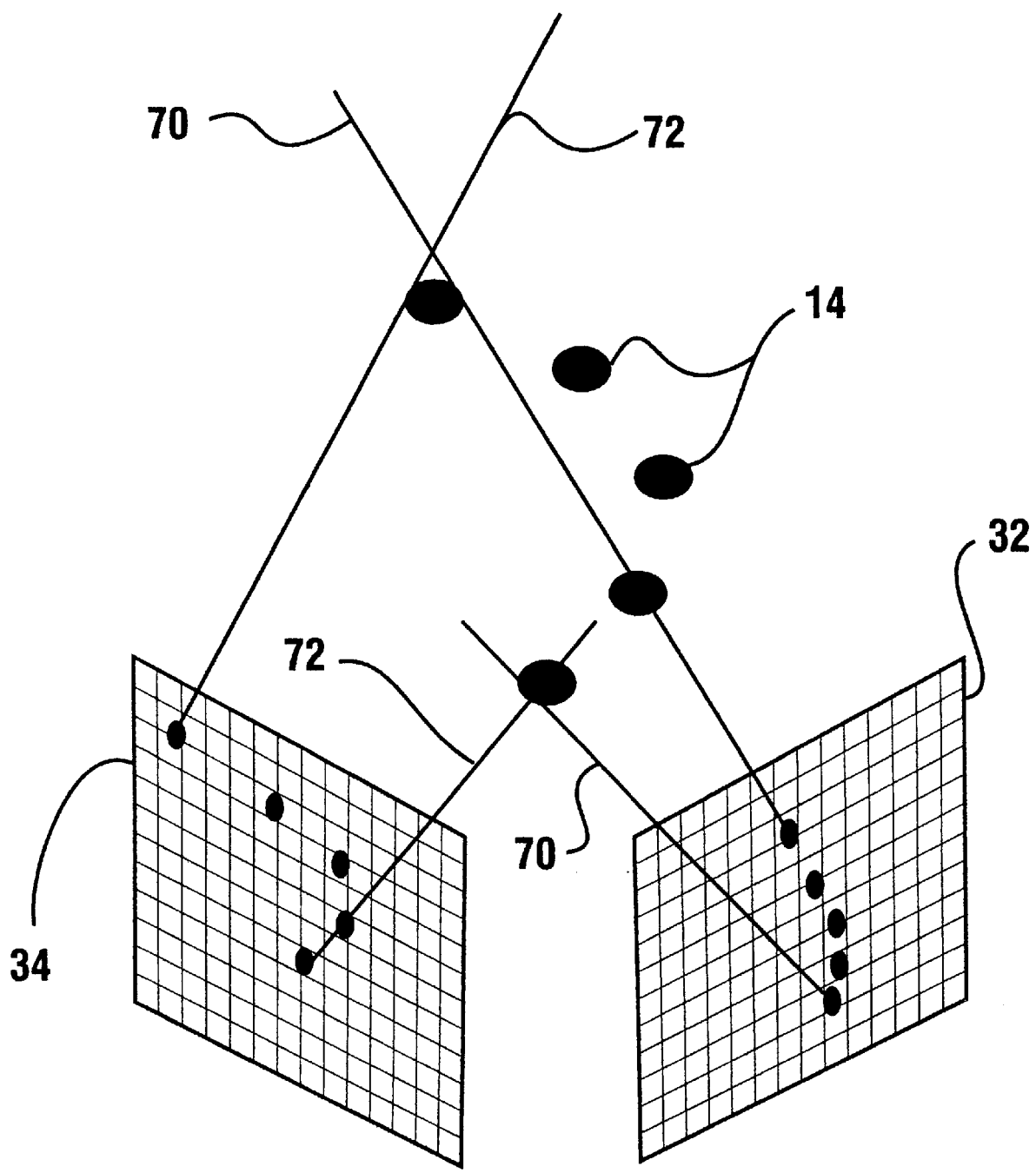
FIG. 5 is an illustration of how a particle's information is employed to stereo match tracks.

Stereo matching is solved by using the same technique in the camera calibration section. It is an inherent part of the camera calibration procedure. FIG. 5 illustrates how the particles information is used to stereo match tracks. First, a track is selected from one camera's pixel array 32 then an attempt is made to stereo match with every track imaged by the other camera's pixel array 34 as illustrated in FIG. 5. The matching is performed between each particle location in the two four-frame tracks represented in FIG. 4. At each location, the three dimensional distance between the two candidate rays 70, 72 is incorporated into a penalty function. The penalty function is described in detail in the paper, P. D. Crouser, M. D. Bethea, and F. L. Merat, "An Evolutionary, Neural Net Model for Globally-Optimized Particle Tracking," presented at the Ohio Aerospace Institute Conference on Neural networks, August, 1995. The farther the rays are from intersecting, the larger the penalty function. The penalty function is accumulated over an entire four-frame track. After comparing penalty functions for matches between one track in the left camera with every track in the right camera, we choose the match with the lowest penalty as a correct match. At this point, the three-dimensional coordinates are calculated at the locations of the nearest intersection of the optical rays. While theoretically the lines 70, 72 should intersect, this never occurs due to the finite precision with which particles can be located in two dimensions. The three dimensional coordinates are calculated for each of the four time steps in the matched track to obtain three-dimensional, quantitative, time dependent information about the flow.

The stereo imaging velocimeter in accordance with the present invention permits the collection of quantitative, three-dimensional flow data from any optically transparent fluid which can be seeded with tracer particles. This provides a means to measure three-dimensional fluid velocities quantitatively and qualitatively at a plurality of points. The stereo imaging velocimetry of the present invention is applicable to any system with an optically transparent fluid seeded with tracer particles. While one particular interest of the present application in stereo imaging velocimetry is focused on its potential for use in microgravity experiments performed for the space shuttle, there are many other uses for this technology known to those skilled in this art. Except for the tracer particles, this measurement technique is non-intrusive. Stereo imaging velocimetry can benefit many fields of study including computer vision, image processing, biomedical imaging, fluid physics and any transparent medium that can be seeded with tracer particles.

The system of the present invention provides three-dimensional, full-field, quantitative and qualitative vectors from two or more cameras aligned approximately perpendicular with respect to each other. This is a vast improvement over similar systems as it quantifies the entire field of view, not just a subset of a view.

The system of the present invention does not require lasers or highly specialized optics. It uses off-the-shelf hardware with no special features in order to implement stereo imaging velocimetry. The present invention has a general purpose so that it can be used in several different fields of technology. It can be applied to any existing technology or an experiment using multiple cameras. The system and method provides an accuracy to within 2% of a full-field which is many times greater than prior art systems or methods.

In the foregoing description, certain terms have been used for brevity, clarity and understanding. However, no unnecessary limitations are to be implied therefrom because such terms are for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means capable of performing the recited function. It shall not be deemed to be limited to the particular means shown in the foregoing description or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations, methods, processes and relationships are set forth in the appended claims.

We claim:

1. A method for measuring three-dimensional velocities at a plurality of points in a fluid, comprising the steps of:
   positioning at least two cameras to view a fluid with the cameras being approximately perpendicular to one another;
   defining a coordinate system for each camera based on a world coordinate system;
   recording a two-dimensional view of the fluid seeded with tracer particles for each camera;
   determining centroid coordinates from the two dimensional images of the tracer particles;
   determining tracer particle tracks as viewed by each camera based upon the determined centroid coordinates; and
   stereo matching the two dimensional tracer particle tracks between the camera views for finding three-dimensional locations of the tracer particles as a function of time and measuring velocities thereof.

2. A method according to claim 1, wherein the step of determining centroid coordinates further comprises the step of decomposing overlapping tracer particles into constituent centroids.

3. A method according to claim 2, wherein the decomposing overlapping tracer particles step includes the step of using major axis length and circumference for recognizing overlapping tracer particles.

4. A method according to claim 3, wherein the tracer particle tracks determining step includes the step of tracking tracer particles in a four frame sequence.

5. A method according to claim 4, further comprising the steps of performing a consistency check on a calculated velocity field and discarding any tracer particle tracks which are in a determined disagreement with neighboring tracer particle tracks.

6. A method according to claim 1, wherein the defining step comprises the steps of:
   situating an origin at approximately a center of an imaged fluid volume where principal optical axes of the cameras have a point of nearest intersection; and
   providing each camera with its own coordinate system tied to its image plane.

7. A method according to claim 1, further comprising the step of calibrating each camera by imaging a calibration target plane containing calibration points.

8. A method according to claim 7, wherein the calibrating step further comprises the steps of:
   calibrating a left and a right camera view separately; and
   combining both views to produce a three-dimensional view.

9. A method according to claim 7, wherein the calibrating step comprises the steps of:
   (a) choosing positions of a number of calibration points in a fluid volume using coordinates x, y, z;
   (b) determining exact pixel locations of the calibration points for each camera by employing a physical model;
   (c) choosing values of all the camera parameters to input into the physical model;
   (d) adding a random amount of error value to calculated pixel locations in order to obtain pseudo experimental pixel values;
   (e) inputting coordinates and pseudo experimental pixel values of the number of calibration points into a least squares fitting procedure to obtain pseudo experimental camera parameters;
   (f) comparing pseudo experimental camera parameters with the chosen values for the camera parameters;
   (g) adding new random error values to the calculated pixel positions and redoing steps (e) and (f);
   (h) changing the number of calibration points and redoing steps (a)–(g);
   (i) changing the positions of the number of calibration points, and redoing steps (a)–(h); and
   (j) using data generated from the above steps to obtain camera calibration coefficients based upon a best fit analysis.

10. A method according to claim 4, wherein the stereo matching step includes the step of providing a penalty function at each tracer particle location, wherein at each location a three-dimensional distance between two optical rays is incorporated into the penalty function so that the farther the optical rays are from intersecting the larger the penalty function.

11. A method according to claim 10, further comprising the step of comparing penalty functions for matches between one track in a left camera with every track in a right camera to choose the match with the lowest penalty function as a correct match.

12. A method according to claim 1, wherein the fluid is an optically transparent fluid.

13. A method according to claim 1, wherein the at least two cameras are CCD cameras operating with an every-other line scan pattern.

14. A system for measuring three-dimensional velocities at a plurality of points in a fluid, comprising:
   at least two cameras positioned to view a fluid seeded with tracer particles, said at least two cameras being positioned approximately perpendicular to one another, said at least two cameras providing two-dimensional views of the tracer particles seeded in the fluid;
   signal processing means connected to said at least two cameras for receiving and recording the two-dimensional views;
   centroid determining means connected to and in communication with said signal processing means for accurately locating a centroid of each tracer particle in a frame and establishing coordinates therefor;

means for decomposing overlapping tracer particle clusters into constituent centroids connected to and in communication with said signal processing means and said centroid determining means;

means for tracer particle tracking of the velocity of individual tracer particle images connected to and in communication with said signal processing means, said centroid determining means, and said overlapping tracer particle decomposing means, said tracer particle tracking means determining a correspondence between individual tracer particles over time and across orthogonal views to track in two dimensions; and means for stereo matching connected to and in communication with said signal processing means, said centroid determining means, said overlapping tracer particle decomposing means and said tracer particle tracking means;

said stereo matching means determining which individual tracer particle images from synchronized images represent identical tracer particles; said stereo matching means calculating three-dimensional coordinates from the two-dimensional coordinates as a function of time and distance of the tracer particles in the fluid stream for measuring the three-dimensional velocities at the plurality of points in the fluid.

15. A system according to claim 14, wherein the fluid is an optically transparent fluid.

16. A system according to claim 14, wherein said at least two cameras comprise CCD cameras.

17. A system according to claim 14, wherein said at least two cameras comprise CID cameras.

18. A system according to claim 14, wherein said signal processing means comprises a laser disk recorder.

19. A system for collecting quantitative, three-dimensional flow data from an optically transparent fluid having tracer particles, comprising:

at least two cameras situated approximately perpendicular to one another for viewing the fluid with tracer particles;

image analysis means connected to said at least two cameras for receiving and recording two-dimensional views therefrom; and a computer connected to said image analysis means and in communication therewith, said computer first determining a centroid with coordinates for each tracer particle and then determining tracer particle tracks as viewed by each camera from the centroid coordinates, said computer generating three-dimensional locations of the tracer particles as a function of time with means for stereo matching between camera views to collect quantitative, three-dimensional flow data.

20. A system according to claim 19, wherein said computer further includes means for decomposing overlapping tracer particle clusters into constituent centroids.

* * * * *